(12) United States Patent
Hong et al.

(10) Patent No.: US 6,776,794 B1
(45) Date of Patent: Aug. 17, 2004

(54) STENT PATTERN WITH MIRROR IMAGE

(75) Inventors: James Hong, San Jose, CA (US); Sharon Segvich, Crown Point, IN (US); E Tina Cheng, Union City, CA (US); Napoleon Caliguiran, Union City, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 321 days.

(21) Appl. No.: 09/997,828

(22) Filed: Nov. 28, 2001

(51) Int. Cl.[7] .................................................. A61F 2/06
(52) U.S. Cl. ...................................................... 623/1.15
(58) Field of Search .............................. 623/1.15–1.17, 623/1.1, 1.12, 1.35, 23.71, 901; 606/194–195, 200

(56) References Cited

U.S. PATENT DOCUMENTS

| | | | |
|---|---|---|---|
| 6,106,548 A | 8/2000 | Roubin et al. | |
| 6,344,055 B1 * | 2/2002 | Shukov | 623/1.15 |
| 6,565,598 B1 * | 5/2003 | Lootz | 623/1.15 |
| 6,626,935 B1 * | 9/2003 | Ainsworth et al. | 623/1.15 |
| 2001/0044652 A1 | 11/2001 | Moore | |
| 2001/0044653 A1 | 11/2001 | Moore | |
| 2002/0007212 A1 | 1/2002 | Brown et al. | |
| 2002/0023843 A1 | 2/2002 | Cherkes | |
| 2002/0032478 A1 | 3/2002 | Boekstegers et al. | |
| 2002/0042647 A1 | 4/2002 | Jang | |
| 2002/0045933 A1 | 4/2002 | Jang | |
| 2002/0045934 A1 | 4/2002 | Jang | |
| 2002/0045935 A1 | 4/2002 | Jang | |
| 2002/0052646 A1 | 5/2002 | Fischell et al. | |

FOREIGN PATENT DOCUMENTS

WO    WO 02/24111 A2    3/2002

* cited by examiner

Primary Examiner—(Jackie) Tan-Uyen T. Ho
(74) Attorney, Agent, or Firm—Fulwider Patton Lee & Utecht, LLP

(57) ABSTRACT

An expandable stent for implanting in a body lumen, such as a coronary artery, peripheral artery, or other body lumen is provided. An intravascular stent is formed by cylindrical rings connected by links. The rings have peaks and valleys from which extend straight and nonlinear bar arms, forming a figure-eight. An elemental unit is defined with straight and nonlinear bar arms, and elemental units on adjacent rings are mirror images of one another. The links have one end connected at a peak of one ring and the other end connected to a central portion of a nonlinear bar arm. Alternating rows of the links consist of nonlinear links.

33 Claims, 2 Drawing Sheets

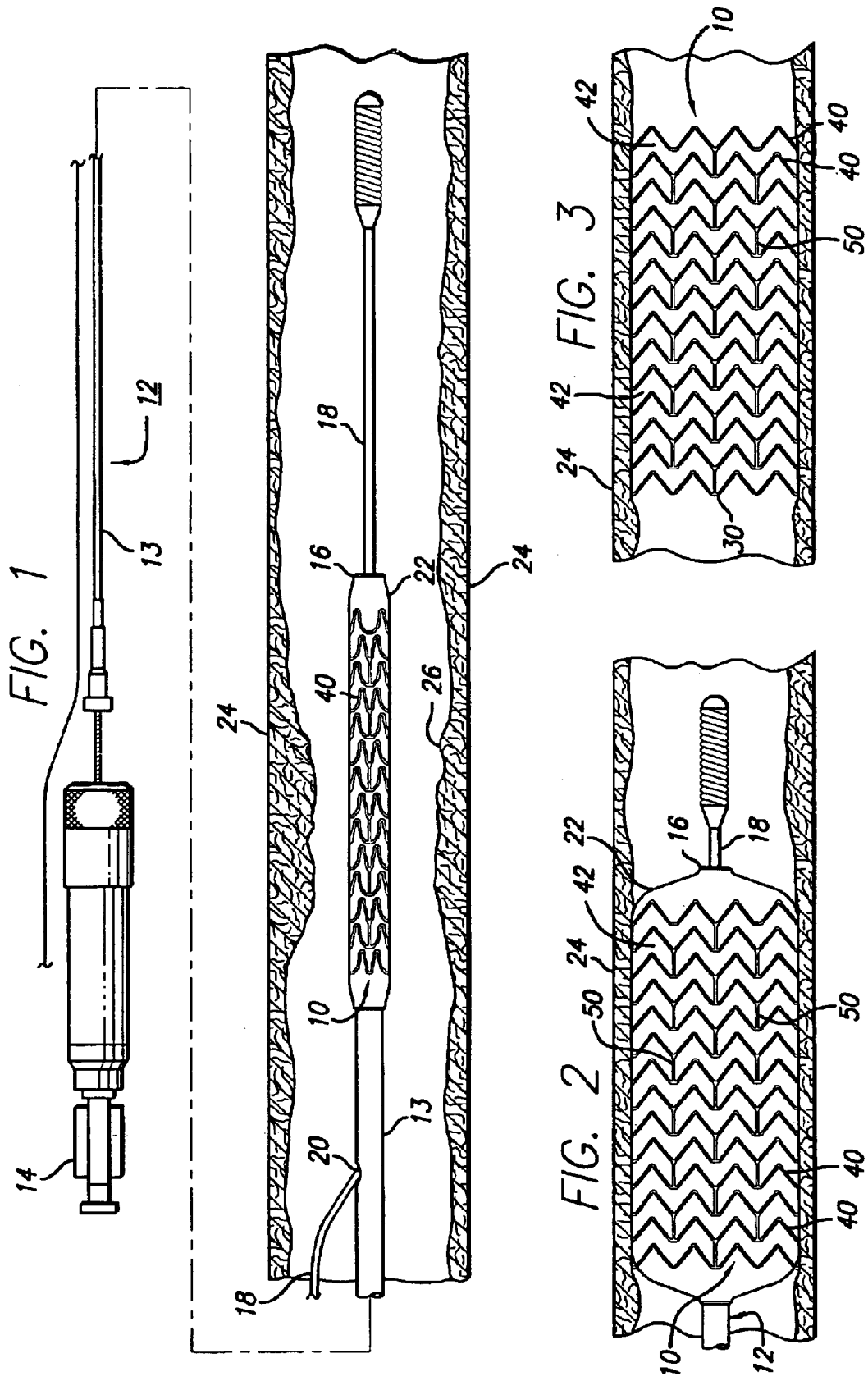

STENT PATTERN WITH MIRROR IMAGE

BACKGROUND OF THE INVENTION

This invention relates to endoluminal prostheses such as vascular repair devices, and in particular intravascular stents, which are adapted to be implanted into a patient's body lumen, such as a blood vessel or coronary artery, to maintain the lumen's patency. Stents are particularly useful in the treatment of atherosclerotic stenosis and are most frequently used in connection with coronary angioplasty.

Stents are tubular, usually cylindrical devices which hold open a segment of blood vessel or other body lumen. They also are suitable to support and hold back a dissected arterial lining that can occlude the lumen. At present, numerous models of stents art marketed throughout the world. While some of these stents are flexible and have the appropriate strength and rigidity needed to hold open a lumen such as a coronary artery, each stent design typically represents a compromise between the stent's flexibility and its radial strength. What has been needed, and heretofore unavailable, is a stent which has a high degree of flexibility so that it can be advanced through tortuous lumen and readily expanded, and yet have the mechanical strength to hold open the lumen or artery into which it is implanted and provide enough stiffness to prevent catheter rotation. Also needed is a stent that provides adequate vessel wall coverage, permits a large expansion range and offers more conformability.

At least some in the stent industry also perceive a problem with "fishscaling." Fishscaling, describes the twisting or bending of stent struts, which results in the struts not conforming to a generally cylindrical plane around the circumference of the stent. Fishscaling can result from the manufacturing process, and also can occur during the stent placement process, such as when portions of the stent surface are forced outward as the stent bends while advancing through tortuous lumen. Some in the stent art believe that fishscaling can damage the blood vessel through which the stent is being advanced. Therefore, there is a perceived need for a stent that reduces or eliminates fishscaling.

SUMMARY OF THE INVENTION

The present invention is directed to an endoluminal prosthesis, such as an intravascular stent, which is highly flexible along its longitudinal axis to facilitate delivery through tortuous body lumens, but which is strong and stable enough radially in its expanded condition to maintain the patency of a body lumen when the stent is implanted therein. The stent also reduces fishscaling, provides more uniform connectivity, and decreases unsupported surface area.

The stent of the present invention includes a plurality of generally cylindrical elements, also known as rings, that are interconnected to form the stent. The stent typically is mounted on a balloon catheter if it is balloon expandable, or it can be mounted on a catheter without a balloon if it is self-expanding.

Each of the cylindrical rings or elements has a proximal end and a distal end and a cylindrical plane defined by a cylindrical outer wall surface that extends circumferentially between the proximal end and the distal end of the cylindrical ring. The rings are aligned along a longitudinal axis, with each having numerous peaks and valleys. These peaks and valleys are defined by adjacent bar arms, including, generally linear and nonlinear bar arms, with the nonlinear bar arms having an undulating shape. The linear bar arms have a first arm axis and the nonlinear bar arms have a second arm axis, the first arm axis is parallel to the longitudinal axis of the stent, and the first and second arm axes are at acute angles to each other. At least one link is used to connect each cylindrical ring to an adjacent ring to form the stent. The links are connected to a central portion of the nonlinear bar arm on one ring and a peak of the adjacent ring.

An embodiment of the invention has alternating rows of at least one link consisting of nonlinear links, while the other rows of at least one link consist of linear links. This design enhances flexibility with the use of the nonlinear links, but also provides stiffness which prevents catheter rotation with the use of the linear links. In this embodiment, the nonlinear links are offset by ninety degrees from the adjacent linear links.

In one embodiment, the peak that is connected to the nonlinear link is defined by a v-shaped bar arm. Alternating cylindrical rings have at least one v-shaped bar arm which forms at least one peak of the ring. In each alternating ring, the v-shaped bar arm is connected to the adjacent nonlinear bar arm on one side, and the adjacent linear bar arm on the other side.

The cylindrical rings define certain patterns, one pattern called a unit, involves one nonlinear bar arm disposed in-between two linear bar arms. In this embodiment, the units on adjacent cylindrical rings are mirror-images of one another. This design with the mirrored units provides more uniform connectivity. Another pattern found in the cylindrical rings, is a ring portion shaped like a figure-eight. The figure-eight portions are defined by a linear bar arm and portions of two non-linear bar arms. Another aspect of the stent design is that the peaks and valleys of one cylindrical ring are separately disposed in-phase with the peaks and valleys of the adjacent cylindrical ring.

Typically, a balloon expandable stent is made from a stainless steel alloy or similar material. The cylindrical rings of the stent are plastically deformed when expanded by the balloon. The cylindrical rings of the stent can expand radially outwardly without a balloon when the stent is formed from a superelastic alloy, such as nickel titanium (NiTi) alloys. These so-called "self-expanding" stents expand upon application of a temperature change or when a stress is relieved, as in the case of a pseudo-elastic phase change.

The number of peaks, valleys, links, and cylindrical rings can be varied as the application requires. When using nonlinear or flexible links, the link typically does not expand when the cylindrical rings of the stent expand radially outwardly, but the links do continue to provide flexibility and to also provide a scaffolding function to assist in holding open the artery. Further, because the links do not expand or stretch when the stent is radially expanded, the overall length of the stent is substantially the same in the unexpanded and expanded configurations. In other words, the stent will not appreciably shorten upon expansion.

The stent can be formed from a tube by laser cutting the pattern of cylindrical rings and flexible links in the tube. The stent also may be formed by laser cutting a flat metal sheet in the pattern of the cylindrical rings and links, and then rolling the pattern into the shape of the tubular stent and providing a longitudinal weld to form the stent

BRIEF DESCRIPTION OF THE DRAWINGS

FIG. 1 is an elevation view, partially in section, of a stent which is mounted on a rapid-exchange delivery catheter and positioned within an artery.

FIG. 2 is an elevation view, partially in section, similar to that shown in FIG. 1, wherein the stent is expanded within the artery so that the stent embeds within the arterial wall.

FIG. 3 is an elevation view, partially in section, showing the expanded stent implanted within the artery after withdrawal of the rapid-exchange delivery catheter.

DETAILED DESCRIPTION OF THE PREFERRED EMBODIMENTS

Figure 4:
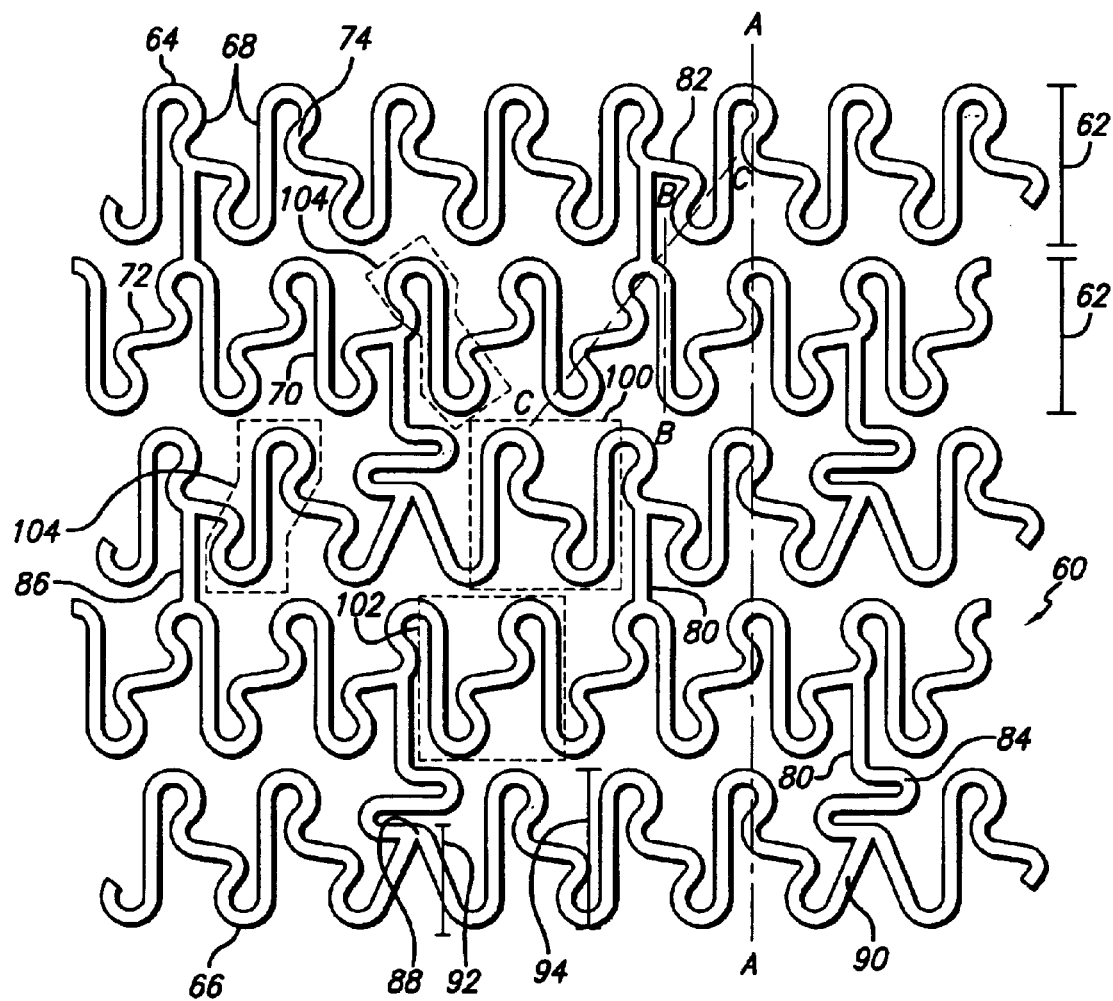
FIG. 4 is a flattened plan view of a stent pattern which illustrates a configuration of the present invention.

The present invention improves on existing endovascular prostheses, such as stents, by providing a decrease in unsupported surface area, and a more flexible device with a uniquely designed ring pattern and novel interconnecting members or links. An aspect of the invention is the arrangement of linear and non-linear bar arms, or struts, which form a figure-eight pattern, and mirrored elemental units. The design of the stent struts and the interconnecting members (also called links or connectors, and, by some in the art, struts) and their placements provide for uniform scaffolding and a high degree of vessel wall coverage.

The present invention includes a specific stent pattern, one embodiment of which is depicted in FIG. 4, and will be discussed in more detail below. The general use of stents will be discussed first in order to lay a foundation for the stent pattern of the present invention.

FIGS. 1–3 can represent any balloon expandable stent 10 with which the various configurations can be used. FIG. 1 depicts a stent 10 with interconnected cylindrical rings 40 mounted on a catheter assembly 12 which is used to deliver the stent 10 and implant it in a body lumen, such as a coronary artery, peripheral artery, or other vessel or lumen within the body. The catheter assembly includes a catheter shaft 13 which has a proximal end 14 and a distal end 16. The catheter assembly is configured to advance through the patient's vascular system by advancing over a guide wire by any of the well-known methods of an over-the-wire system (not shown) or a well-known rapid exchange catheter system, such as the one shown in FIG. 1. The stent 10 in FIGS. 1–3 conceptually represents any type of stent well-known in the art—one comprising a plurality of undulating cylindrical rings 40. An example of such a stent is the Multi-Link Tetra® stent, made by Advanced Cardiovascular Systems, Inc. of Santa Clara, Calif.

Catheter assembly 12 as depicted in FIG. 1 includes an RX (rapid-exchange) port 20 where the guide wire 18 exits the catheter. The distal end of the guide wire 18 exits the catheter distal end 16 so that the catheter advances along the guide wire on a section of the catheter between the RX port 20 and the catheter distal end 16. As is known in the art, the guide wire lumen which receives the guide wire is sized for receiving various diameter guide wires to suit a particular application. The stent is mounted on expandable member 22 (e.g., a balloon) and is crimped tightly thereon, so that the stent and expandable member present a low profile diameter for delivery through the arteries.

As shown in FIG. 1, a partial cross-section of an artery 24 has a small amount of plaque that has been previously treated by angioplasty or other repair procedure. Stent 10 is used to repair a diseased or damaged arterial wall as shown in FIG. 1, or a dissection, or a flap, all of which are commonly found in the coronary arteries and other vessels. The stent 10, and the stent of the present invention, also can be placed and implanted without any prior angioplasty.

In a typical procedure to implant stent 10, the guide wire 18 is advanced through the patient's vascular system by well-known methods, so that the distal end of the guide wire is advanced past the plaque or diseased area 26. Prior to implanting the stent, the cardiologist may wish to perform an angioplasty or other procedure (i.e., atherectomy) in order to open and remodel the vessel and the diseased area. Thereafter, the stent delivery catheter assembly 12 is advanced over the guide wire so that the stent is positioned in the target area. The expandable member or balloon 22 is inflated by well-known means so that it expands radially outwardly and in turn expands the stent radially outwardly until the stent is apposed to the vessel wall. The expandable member is then deflated and the catheter withdrawn from the patient's vascular system. The guide wire typically is left in the lumen for post-dilatation procedures, if any, and subsequently is withdrawn from the patient's vascular system. As depicted in FIGS. 2 and 3, the balloon is fully inflated with the stent expanded and pressed against the vessel wall, and in FIG. 3, the implanted stent remains in the vessel after the balloon has been deflated and the catheter assembly and guide wire have been withdrawn from the patient.

The stent 10 holds open the artery after the catheter is withdrawn, as illustrated by FIG. 3. In one embodiment, the stent is formed from a cylindrical tube with a constant wall thickness, so that the straight and undulating components of the stent are relatively flat in transverse cross-section, so that when the stent is expanded, its flat surface is pressed into the wall of the artery, and as a result does not interfere with the blood flow through the artery. After the stent is pressed into the wall of the artery, it eventually becomes covered with endothelial cell growth which further minimizes blood flow interference. The undulating portion of the stent provides good tacking characteristics to prevent stent movement within the artery. Because the cylindrical rings 40 are closely spaced at regular intervals, they provide uniform support for the wall of the artery, and consequently are well adapted to tack up and hold in place small flaps or dissections in the wall of the artery.

The stent 10 in FIG. 3 has fourteen cylindrical rings 40. The rings are connected by links 50. For the purpose of the present invention, the cylindrical rings 40 could also be connected by links having shapes other than straight, i.e., non-linear links, curved links, welds, or any configuration thereof.

Referring to FIG. 4, a portion of a stent 60 is shown in a flattened condition so that the pattern can be clearly viewed. The stent is typically formed from a tubular member, but it can be formed from a flat sheet such as the portion shown in FIG. 4 and rolled into a cylindrical configuration.

FIG. 4 represents five cylindrical rings 62 of stent 60. The stent can have any number of rings, and the size of the rings may also vary. The cylindrical rings are aligned along a longitudinal axis, which is represented by line A—A. Each cylindrical ring has a cylindrical ring proximal end 64 and a cylindrical ring distal end 66. The proximal ring ends and distal ring ends can also be considered to form a pattern of peaks and valleys, i.e., an undulating shape. The plurality of peaks and valleys are defined by adjacent bar arms 68, including, generally linear or straight bar arms 70 and generally nonlinear bar arms 72. Although the straight bar arms 70 are shown as being linear, it has been contemplated that they may have a curved shape as well. As seen in FIG. 4, the nonlinear bar arms are undulating, and include at least one full, three hundred sixty degree sine wave element 74, which can be symmetrical or skewed. The sinusoidal portion 74 can possess more pointed or more rounded peaks and valleys with more linear connections, like a zigzag shape, and the same is true for the peaks and valleys 64 and 66 of the cylindrical rings. Peaks and valleys are sometimes generically referred to as crests. The selection of which crest is a peak and which crest is a valley is arbitrary and done for ease of reference. Those in the art will understand that, depending upon one's reference, a peak can be a valley, and vice versa. Moreover, those in the art will understand from context the meaning of peak, valley and crest.

Still referring to FIG. 4, the linear bar arms 70 have a first arm axis and the nonlinear bar arms 72 have a second arm axis. For reference, line B—B represents the first arm axis, and line C—C represents the second arm axis. The first arm axis B-B is parallel to the longitudinal axis A-A, and the first and second arm axes B-B and C-C are at acute angles to each other.

There is at least one link 80 connecting each cylindrical ring 62 to an adjacent ring to form the stent 60. The pattern in FIG. 4 shows two links per row that connect the rings together, however, one link or more than 2 links per row could be used to form the stent. In the embodiment shown in FIG. 4, the links are connected to a central portion 82 of the nonlinear bar arm 72 on one ring and a peak 66 of the adjacent ring. Alternating rows of at least one link consist of a nonlinear link 84, while the other rows of at least one link consist of a linear link 86. In this design, the nonlinear links are offset by ninety degrees from the linear links of the adjacent row. The incorporation of nonlinear links in alternating rows enhances flexibility, while the linear links disposed in the remaining rows provide the needed stiffness to prevent catheter rotation. The nonlinear links will not expand when the stent is expanded, and therefore the length of the stent will not change as it is expanded.

In one embodiment, a peak 88 connected to the nonlinear link 84 is defined by a v-shaped bar arm 90 which is connected in-between the adjacent nonlinear bar arm 72 on one side, and the adjacent linear bar arm 70 on its other side. The v-shaped bar arm has a shorter longitudinal length 92 than the longitudinal length 94 of the linear bar arm in order to accommodate the length of the nonlinear link 84, which in this embodiment is longer than linear link 86. The length of the v-shaped bar arm and nonlinear link can increase or decrease proportionally to one another, and the shape of the peak of the v-shaped bar arm can be altered, for example, to a curved or rounded shape.

In the stent pattern of this embodiment, a plurality of units or elemental units 100 are defined by one nonlinear bar arm 72 in-between two linear bar arms 70. As seen in FIG. 4, the units of one cylindrical ring 62 are mirror-images of units 102 on the adjacent ring. This design using the mirrored elemental units provides more uniform connectivity.

The stent pattern in FIG. 4 also results in a number of ring portions 104 shaped like figure-eights. Each figure-eight portion is defined by a linear bar arm 70 and portions of two non-linear bar arms 72. The tops and bottoms of the figure-eight portion are the peaks 66 and valleys 64 of the rings 62. It can be seen in FIG. 4 that the the peak of one cylindrical ring is disposed in-phase with the peak of the adjacent cylindrical ring, and the valley of one cylindrical ring is disposed in-phase with the valley of the adjacent cylindrical ring.

Other embodiments of the invention, although not shown, are easily developed and fall within the scope of the present invention. One link may include more than one non-linear portion. For example, one could create a straight link with two differently shaped apertures. Alternatively, one could combine an undulating link with an aperture. Links or bar arms could have varying thickness. Also, the mirrored elemental units could be defined with bar arms having a variety of shapes including, but not limited to, a zigzag nonlinear bar arm.

The stent of the present invention can be made in many ways. One method of making the stent is to cut a thin-walled tubular member, such as stainless steel tubing, to remove portions of the tubing in the desired pattern for the stent, leaving relatively untouched the portions of the metallic tubing which are to form the stent. In accordance with the invention, it is preferred to cut the tubing in the desired pattern by means of a computer controlled laser equipment, as is well known in the art. Such methods are described in U.S. Pat. Nos. 5,759,192 and 5,780,807 to Saunders, which are incorporated herein by reference in their entirety.

The tubing may be made of suitable biocompatible material such as stainless steel or another metal alloy. The stainless steel tube may be alloy type: 316L SS, special chemistry per ASTM F138-92 or ASTM F139-92 grade 2. The following is a table showing the chemical makeup of type 316L per ASTM F138-92 or ASTM F139-92 stainless steel for surgical implants in weight percent:

| | |
|---|---|
| Carbon (C) | 0.03% max. |
| Manganese (Mn) | 2.00% max. |
| Phosphorous (P) | 0.025% max. |
| Sulphur (S) | 0.010% max. |
| Silicon (Si) | 0.75% max. |
| Chromium (Cr) | 17.00–19.00% |
| Nickel (Ni) | 13.00–15.50% |
| Molybdenum (Mo) | 2.00–3.00% |
| Nitrogen (N) | 0.10% max. |
| Copper (Cu) | 0.50% max. |
| Iron (Fe) | Balance |

The tubing is mounted in a rotatable collet fixture of a machine-controlled apparatus for positioning the tubing relative to a laser. According to machine-encoded instructions, the tubing is rotated and moved longitudinally relative to the laser, which is also machine controlled. The laser selectively removes the material from the tubing by ablation, thereby cutting a pattern into the tube.

The process of cutting a stent pattern into the tubing is automated, except for loading and unloading the length of tubing. In one example, a CNC opposing collet fixture for axial rotation of the length of tubing is used in conjunction with a CNC X/Y table to move the length of tubing axially relatively to a machine-controlled laser. The entire space between collets can be patterned using the $CO_2$ laser set-up of the foregoing example. The program for control of the apparatus is dependent on the particular configuration used and the pattern to be ablated in the coating.

Cutting a fine structure (e.g., a 0.0035 inch web width) requires minimal heat input and the ability to manipulate the tube with precision. It is also necessary to support the tube yet not allow the stent structure to distort during the cutting operation. In order to successfully achieve the desired end results, the entire system must be configured very carefully. The tubes for coronary stents are made typically of stainless steel with an outside diameter of 0.060 inch to 0.066 inch and a wall thickness of 0.002 inch to 0.004 inch. Dimensions for peripheral stents and other endoluminal prostheses may be different. These tubes are fixtured under a laser and positioned utilizing CNC equipment to generate a very intricate and precise pattern. Due to the thin wall and the small geometry of the stent pattern, it is necessary to have very precise control of the laser, its power level, the focused spot size, and the precise positioning of the laser cutting path.

Minimizing the heat input into the stent structure prevents thermal distortion, uncontrolled burn out of the metal, and metallurgical damage due to excessive heat, and thereby produces a smooth debris free cut. A Q-switched Nd-YAG, typically available from Quantronix of Hauppauge, N.Y., is utilized. The frequency is doubled to produce a green beam at 532 nanometers. Q-switching produces very short pulses (<100 nS) of high peak powers (kilowatts), low energy per pulse ($\leq 3$ mJ), at high pulse rates (up to 40 kHz). The frequency doubling of the beam from 1.06 microns to 0.532 microns allows the beam to be focused to a spot size that is 2 times smaller, therefore increasing the power density by a factor of 4 times. With all of these parameters, it is possible to make smooth, narrow cuts in the stainless tubes in very fine geometries without damaging the narrow struts that make up the stent structure. The system makes it possible to adjust the laser parameters to cut a narrow kerf width, which minimizes the heat input into the material.

The positioning of the tubular structure requires the use of precision CNC equipment, such as that manufactured and sold by Aerotech Corporation. In addition, a unique rotary mechanism has been provided that allows the computer program to be written as if the pattern were being cut from a flat sheet. This allows both circular and linear interpolation to be utilized in programming.

The optical system, which expands the original laser beam, delivers the beam through a viewing head and focuses the beam onto the surface of the tube. It incorporates a coaxial gas jet and nozzle that help to remove debris from the kerf and cool the region where the beam cuts and vaporizes the metal. It is also necessary to block the beam as it cuts through the top surface of the tube and prevent the beam, along with the molten metal and debris from the cut, from impinging on the opposite, inner surface of the tube.

In addition to the laser and the CNC positioning equipment, the optical delivery system includes: a beam expander to increase the laser beam diameter; a circular polarizer, typically in the form of a quarter wave plate, to eliminate polarization effects in metal cutting; provisions for a spatial filter; a binocular viewing head and focusing lens; and, a coaxial gas jet that provides for the introduction of a gas stream that surrounds the focused beam and is directed along the beam axis. The coaxial gas jet nozzle (0.018 inch I.D.) is centered around the focused beam with approximately 0.010 inch between the tip of the nozzle and the tubing. The jet is pressurized with oxygen at 20 psi and is directed at the tube with the focused laser beam exiting the tip of the nozzle (0.018 inch dia.). The oxygen reacts with the metal to assist in the cutting process, similar to oxyacetylene cutting. The focused laser beam acts as an ignition source and controls the reaction of the oxygen with the metal. In this manner, it is possible to cut the material with a very fine, precise kerf. In order to prevent burning by the beam and/or molten slag on the far wall of the tube I.D., a stainless steel mandrel (approx. 0.034 inch dia.) is placed inside the tube and is allowed to roll on the bottom of the tube as the pattern is cut. This acts as a beam/debris block protecting the far wall I.D.

Alternatively, burning may be prevented by inserting a second tube inside the stent tube. The second tube has an opening to trap the excess energy in the beam, which is transmitted through the kerf and which collects the debris that is ejected from the laser cut kerf. A vacuum or positive pressure can be placed in this shielding tube to remove the collection of debris.

Another technique that could be utilized to remove the debris from the kerf and cool the surrounding material would be to use the inner beam blocking tube as an internal gas jet. By sealing one end of the tube and making a small hole in the side and placing it directly under the focused laser beam, gas pressure could be applied, creating a small jet that would force the debris out of the laser cut kerf from the inside out. This would eliminate any debris from forming or collecting on the inside of the stent structure. It would place all the debris on the outside. With the use of special protective coatings, the resultant debris could be easily removed.

In most cases, the gas utilized in the jets may be reactive or non-reactive (inert). In the case of reactive gas, oxygen or compressed air is used. Compressed air is used in this application since it offers more control of the material removed and reduces the thermal effects of the material itself. Inert gas such as argon, helium, or nitrogen can be used to eliminate any oxidation of the cut material. The result is a cut edge with no oxidation, but there is usually a tail of molten material that collects along the exit side of the gas jet that must be mechanically or chemically removed after the cutting operation.

The cutting process utilizing oxygen with the finely focused green beam results in a very narrow kerf (approx. 0.0005 inch) with the molten slag re-solidifying along the cut. This traps some scrap, thus requiring further processing. In order to remove the slag debris from the cut, it is necessary to soak the cut tube in a solution of HCL for approximately eight minutes at a temperature of approximately 55° C. Before it is soaked, the tube is placed in an alcohol and water bath and ultrasonically cleaned for approximately one minute. This removes the loose debris left from the cutting operation. After soaking, the tube is then ultrasonically cleaned in the heated HCL for one to four minutes, depending upon the wall thickness. To prevent cracking or breaking of the struts attached to the material left at the two ends of the stent pattern due to harmonic oscillations induced by the ultrasonic cleaner, a mandrel is placed down the center of the tube during the cleaning and scrap removal process. At the completion of this process, the stent structure is rinsed in water and is now ready for electropolishing.

The stents are preferably electrochemically polished in an acidic aqueous solution such as a solution of ELECTRO-GLO#300, sold by ELECTRO-GLO Co., Inc,. Chicago, Ill., which is a mixture of sulfuric acid, carboxylic acid, phosphates, corrosion inhibitors and a biodegradable surface active agent. The bath temperature is maintained at about 110°–135° F. and the current density is about 0.4 to about 1.5 amps per in.$^2$.

Cathode to anode area should be at least about two to one. The stents may be further treated if desired, for example by applying a biocompatible coating.

It will be apparent that both focused laser spot size and depth of focus can be controlled by selecting beam diameter and focal length for the focusing lens. It will be apparent that increasing laser beam diameter, or reducing lens focal length, reduces spot size at the cost of depth of field.

Direct laser cutting produces edges which are essentially perpendicular to the axis of the laser cutting beam, in contrast with chemical etching and the like which produce pattern edges which are angled. Hence, the laser cutting process essentially provides strut cross-sections, from cut-to-cut, which are square or rectangular, rather than trapezoidal. The struts have generally perpendicular edges formed by the laser cut. The resulting stent structure provides superior performance.

Other methods of forming the stent of the present invention can be used, such as chemical etching; electric discharge machining; laser cutting a flat sheet and rolling it into a cylinder; and the like, all of which are well known in the art at this time.

The stent of the present invention also can be made from metal alloys other than stainless steel, such as shape memory alloys. Shape memory alloys are well known and include, but are not limited to titanium, tantalum, nickel titanium and nickel/titanium/vanadium. Other suitable materials include copper-tin, copper-zinc, copper-zinc-tin, copper-zinc-xenon, copper-aluminum-nickel, copper-gold-zinc, gold-cadmium, gold-copper-zinc, iron beryllium ($Fe_3Be$), iron platinum ($Fe_3Pt$), indium-thallium, iron-manganese, iron-nickel-titanium-cobalt, and silver-cadmium. Any of the superelastic or shape memory alloys can be formed into a tube and laser cut in order to form the pattern of the stent of the present invention. As is well known, the superelastic or shape memory alloys of the stent of the present invention can include the type known as thermoplastic martensitic transformation, or display stress-induced martensite. These types of alloys are well known in the art and need not be further described here.

Importantly, a stent formed of shape memory or superelastic alloys, whether the thermoelastic or the stress-induced martensite-type, can be delivered using a balloon catheter of the type described herein, or in the case of stress induced martensite, be delivered via a sheath catheter or a catheter without a balloon.

While the invention has been illustrated and described herein in terms of its use as an intravascular stent, it will be apparent to those skilled in the art that the stent can be used in other body lumens. Further, particular sizes and dimensions, the configuration of undulations, number of crowns per ring, materials used, and other features have been described herein and are provided as examples only. Other modifications and improvements may be made without departing from the scope of the invention. For example, the cylindrical rings can be octagonal, hexagonal, or some other polygon, thus possessing corners. Each ring is essentially a short tube, (or hoop or ring) whose length is preferably shorter than its diameter and which has a significant percentage of the tube surface removed. Other modifications could include the use of polymers in portions of the links and/or bar arms so that the stent would be more radiopaque. Alternatively, one could place electrical discontinuities in the stent to minimize the Faraday Cage effect and make the stent more visible under Magnetic Resonance Imaging.

While a particular form of the invention has been illustrated and described, it will also be apparent to those skilled in the art that various modifications can be made without departing from the spirit and scope of the invention. The present invention is not limited to stents for any particular body lumen, and may also be used in the design of grafts as well. The size of the stent can vary in terms of inner diameter, outer diameter, wall thickness and length. Accordingly, it is not intended that the invention be limited except by the appended claims.

What is claimed is:

1. An intravascular stent for use in a body lumen, comprising:
a plurality of cylindrical rings aligned along a longitudinal axis, each ring having a plurality of peaks and valleys, with the peaks and valleys formed by adjacent bar arms, including, generally linear bar arms and generally nonlinear bar arms; and
at least one link connecting each cylindrical ring to an adjacent ring to form the stent;
the nonlinear bar arms having an undulating member;
the linear bar arms having a first arm axis and the nonlinear bar arms having a second arm axis, with the first and second arm axes being at acute angles to each other; and
wherein the at least one link connects to a central portion of the nonlinear bar arm on one ring and a peak of the adjacent ring, and at least one peak connected to a nonlinear link being formed by a v-shaped bar arm, the v-shaped bar arm being disposed between the nonlinear bar arm and the linear bar arm, the v-shaped bar arm having a shorter longitudinal length than the longitudinal length of the linear bar arm.

2. The stent of claim 1, wherein alternating rows of at least one link have nonlinear links, and the rows of at least one link adjacent to the nonlinear links have linear links.

3. The stent of claim 2, wherein the nonlinear links being offset by ninety degrees from the adjacent linear links.

4. The stent of claim 1, wherein one nonlinear bar arm in-between two linear bar arms form a unit.

5. The stent of claim 4, wherein units on adjacent cylindrical rings mirror one another.

6. The stent of claim 1, wherein each cylindrical ring comprises ring portions shaped like figure-eights.

7. The stent of claim 6, wherein the figure-eight portions comprise a linear bar arm and portions of two non-linear bar arms.

8. The stent of claim 1, wherein the peaks and valleys of one cylindrical ring being separately disposed in-phase with the peaks and valleys of the adjacent cylindrical ring.

9. The stent of claim 1, wherein the first arm axis being parallel to the longitudinal axis.

10. The stent of claim 1, wherein the second arm axis is neither parallel nor perpendicular to the longitudinal axis.

11. The stent of claim 1, wherein a portion of one ring having a linear bar arm connected to a nonlinear bar arm is a mirror image of a portion on the adjacent ring having a linear bar arm connected to a nonlinear bar arm.

12. The stent of claim 11, wherein the mirror image is along the longitudinal axis.

13. The stent of claim 11, wherein the mirror image is along a circumferential axis.

14. The stent of claim 1, wherein each cylindrical ring comprises ring portions shaped like figure-eights, the figure-eight portion formed of a strut configuration having two loops, the end of one loop pointing toward the other loop.

15. The stent of claim 14, wherein the figure-eight portions comprise a linear bar arm and portions of two non-linear bar arms.

16. An expandable endovascular prosthesis, comprising:
a plurality of adjacent, expandable, undulating rings comprised of peaks and valleys, the peaks and valleys being formed by straight bar arms and nonlinear bar arms;
a plurality of links connecting adjacent rings, the links being connected to a central portion of the nonlinear bar arm on one ring and a peak of the adjacent ring;
wherein each ring comprises a plurality of elemental units, each elemental unit formed by one nonlinear bar arm in-between two straight bar arms;
wherein the elemental units of adjacent rings are mirror-images of one another; and
wherein at least one peak connected to a nonlinear link is formed by a v-shaped bar arm, and the v-shaped bar arm being connected to the adjacent nonlinear bar arm and the adjacent linear bar arm, the v-shaped bar arm having a shorter longitudinal length than the longitudinal length of the linear bar arm.

17. The prosthesis of claim 16, wherein each ring further comprises ring portions shaped like figure-eights.

18. The prosthesis of claim 17, wherein the figure-eight portions being defined by one straight bar arm and portions of two nonlinear bar arms.

19. The prosthesis of claim 16, wherein alternating rows of links have nonlinear links.

20. The prosthesis of claim 19, wherein alternating rows of links consist of have linear links.

21. The prosthesis of claim 16, wherein links of adjacent rows being offset by ninety degrees from one another.

22. The prosthesis of claim 16, wherein the peaks and valleys of one ring being separately disposed in-phase with the peaks and valleys of the adjacent ring.

23. A method for inserting an intravascular stent into a vascular lumen, the intravascular stent including a plurality of connected cylindrical rings, the cylindrical rings having peaks and valleys formed by linear and nonlinear bar arms, elemental units defined by one nonlinear bar arm and two linear bar arms, the elemental units of adjacent cylindrical rings mirror one another, and the rings being connected by links, the links being connected to a central portion of the nonlinear bar arm and a peak of the adjacent ring, wherein at least one peak connected to a nonlinear link is formed by a v-shaped-bar arm, the v-shaped bar arm being connected to the adjacent nonlinear bar arm and the adjacent linear bar arm, the v-shaped bar arm having a shorter longitudinal length than the longitudinal length of the linear bar arm, comprising:

mounting the intravascular stent onto a catheter in an unexpanded configuration;

advancing the catheter in the vasculature to position the unexpanded intravascular stent in a desired location in the vascular lumen;

expanding the cylindrical rings of the intravascular stent radially outward;

implanting the intravascular stent in the vascular lumen; and withdrawing the catheter from the vascular lumen.

24. The method of claim 23, wherein the intravascular stent is mounted on an expandable member of the catheter.

25. A method for forming a stent, the stent having a pattern, comprising:

providing a stent pattern having a plurality of connected cylindrical rings, the cylindrical rings having peaks and valleys formed by linear and nonlinear bar arms, elemental units defined by one nonlinear bar arm and two linear bar arms, the elemental units of adjacent cylindrical rings mirror one another, and the rings being connected by links, the links being connected to a central portion of the nonlinear bar arm and a peak of the adjacent ring, wherein at least one peak connected to a nonlinear link is formed by a v-shaped bar arm, the v-shaped bar arm being connected to the adjacent nonlinear bar arm and the adjacent linear bar arm, the v-shaped bar arm having a shorter longitudinal length than the longitudinal length of the linear bar arm; and laser cutting the stent pattern in a tube.

26. The method of claim 25, wherein the stent pattern is laser cut into a tube made of a biocompatible material.

27. The method of claim 25, wherein the stent pattern is laser cut into a tube made of stainless steel.

28. A method for forming a stent, the stent having a pattern comprising a plurality of connected cylindrical rings, the cylindrical rings having peaks and valleys formed by linear and nonlinear bar arms, elemental units defined by one nonlinear bar arm and two linear bar arms, the elemental units of adjacent cylindrical rings mirror one another, and the rings are connected by links, the links being connected to a central portion of the nonlinear bar arm and a peak of the adjacent ring, wherein at least one peak connected to a nonlinear link is formed by a v-shaped bar arm, the v-shaped bar arm being connected to the adjacent nonlinear bar arm and the adjacent linear bar arm, the v-shaped bar arm having a shorter longitudinal length than the longitudinal length of the linear bar arm, comprising:

laser cutting the stent pattern in a flat metal sheet;

rolling the cut metal sheet into a tube; and providing a longitudinal weld along the tube to form the stent.

29. The method of claim 28, wherein the stent pattern is laser cut into a flat metal sheet made of a biocompatible material.

30. The method of claim 28, wherein the stent pattern is laser cut into a flat metal sheet made of stainless steel.

31. An intravascular stent, comprising:

a plurality of cylindrical rings, the cylindrical rings having elemental units defined by a nonlinear bar arm and two linear bar arms, the elemental units of adjacent cylindrical rings mirror one another;

means for connecting the plurality of cylindrical rings together, the means for connecting the plurality of cylindrical rings including at least one link between adjacent rings, the link being connected to a central portion of the nonlinear bar arm on one ring and a peak of the adjacent ring, and at least one peak connected to a nonlinear link being formed by a v-shaped bar arm, the v-shaped bar arm being disposed between the nonlinear bar arm and the linear bar arm, the v-shaped bar arm having a shorter longitudinal length than the longitudinal length of the linear bar arm, means for preventing catheter rotation during use; and means for enhancing flexibility.

32. The stent of claim 31, wherein the means for preventing catheter rotation during use includes the use of linear links to connect adjacent cylindrical rings.

33. The stent of claim 31, wherein the means for enhancing flexibility includes using alternating rows of nonlinear links to connect adjacent cylindrical rings.

* * * * *

UNITED STATES PATENT AND TRADEMARK OFFICE
CERTIFICATE OF CORRECTION

PATENT NO. : 6,776,794 B1
DATED : August 17, 2004
INVENTOR(S) : James Hong et al.

It is certified that error appears in the above-identified patent and that said Letters Patent is hereby corrected as shown below:

Title page,
Item [75], Inventors, delete "E Tina Cheng" and insert -- E. Tina Cheng --.

Column 11,
Line 12, delete "consist of".

Signed and Sealed this

Twenty-fifth Day of January, 2005

JON W. DUDAS
*Director of the United States Patent and Trademark Office*